United States Patent [19]
Boguslawski et al.

[11] Patent Number: 5,118,623
[45] Date of Patent: Jun. 2, 1992

[54] BLEACH STABLE ENZYMES

[75] Inventors: George Boguslawski, South Bend; John W. Shultz, Elkhart, both of Ind.

[73] Assignee: Solvay Enzymes, Inc., Houston, Tex.

[21] Appl. No.: 199,511

[22] Filed: May 27, 1988

[51] Int. Cl.$^5$ .................. C12N 9/56; C12N 15/57; C11D 1/00

[52] U.S. Cl. .................. 435/222; 435/220; 435/221; 252/174.12; 935/10; 935/14

[58] Field of Search .............. 435/219, 220, 222; 252/174.12; 935/10, 14

[56] References Cited

U.S. PATENT DOCUMENTS 3,623,957  11/1971  Feldman ............... 435/222

FOREIGN PATENT DOCUMENTS 130756  1/1985  European Pat. Off. ............ 435/195

OTHER PUBLICATIONS

Estell et al. *Journal of Biol. Chem.* 260(11):6518-21 1985.
Stauffer and Etson, *Journal of Biol. Chem.* 244(19) 5333-38, 1969.

*Primary Examiner*—Elizabeth C. Weimar
*Assistant Examiner*—Keith D. Hendricks
*Attorney, Agent, or Firm*—Willian Brinks Olds Hofer Gilson & Lione

[57] ABSTRACT

The methods of the invention can be used to identify sites of cleavage of an enzyme in the presence of hypochlorite. It has been found that such cleavage occurs at tryptophan. Chemical modifications or genetic manipulation to change or delete tryptophan can be done to produce a more stable enzyme which retains activity in the presence of hypochlorite. The invention is particularly applicable to alkaline proteases which are useful in detergent compositions.

6 Claims, 4 Drawing Sheets

BLEACH STABLE ENZYMES

FIELD OF THE INVENTION

The invention relates to stabilization of enzymes to cleavage at tryptophan in the presence of hypochlorite.

In particular, the invention relates to a bleach stable alkaline protease, a method of identifying the site of cleavage of an alkaline protease by hypochlorite and a method of conferring resistance to cleavage at tryptophan by hypochlorite. Alkaline proteases produced are useful in detergent compositions which can be used in the presence of hypochlorite (chlorine bleach) for stain removal.

BACKGROUND OF THE INVENTION

Hypochlorite is defined herein to include any bleach such as Clorox ® which generate hypochlorite anion, $OCl^-$, upon addition to water and any hypochlorite generated by mixing chlorine in water as shown below:

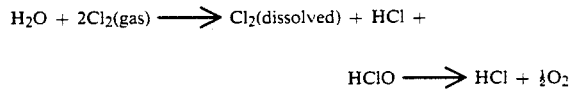

In alkaline solution:

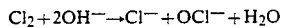

Many enzymes have been found to be inactivated in the presence of chlorine. For example, a paper by Waku et al, CA 78(17):107533p, discloses the inactivation of digestive enzymes trypsin, chymotrypsin, pepsin, pancreatic amylase and pancreatic RNase in concentrations as small as 0.2 ppm of free chlorine.

Enzymes such as proteases are widely used in industrial settings. Inactivation at this low concentration of chlorine could then occur if chlorinated city water is used to clean industrial production equipment. In the dairy or brewing industry, city water, sometimes with the addition of Clorox ® bleach, is used in cleaning equipment. Even a low concentration of hypochlorite left in such equipment could inactivate the proteases used to prepare cheese, yogurt or other fermented milk products.

A specific example of enzyme inactivation in the presence of hypochlorite is found in alkaline proteases which are well known detergent additives. These proteases are sensitive to oxidation. Most are inactivated by very low concentrations of bleach and some are even inactivated by so called "color safe" bleaches, i.e. perborate and peroxy bleaches.

Suggestions have been made to improve the properties of alkaline proteases by site directed mutagenesis. In European Patent Application 0130756 published Jan. 9, 1985, a method for preparing an improved carbonyl hydrolase by site directed mutagenesis was disclosed. The application suggests that oxidative stability, pH activity profiles, $K_m$, $k_{cat}$, $k_{cat}/K_m$ ratios and substrate specificity can be improved by the substitution, deletion or insertion of at least one amino acid at a predetermined site in the hydrolase. Specifically it was suggested that enhanced oxidative stability can be effected by deleting one or more methionine, tryptophan, cysteine or lysine residues and, optionally, substituting another amino acid residue not one of methionine, tryptophan, cysteine or lysine, preferably alanine but alternatively neutral residues.

However, alkaline proteases contain from about 250 to about 290 amino acids and may contain 15 to 18 sites which fit the description above. It would require an inordinate amount of experimentation to perform site directed mutagenesis at each of those sites and to express and test each substitution for improved oxidative stability.

The method of this invention provides a means to identify a site of oxidative cleavage and has been used to identify a specific residue which can be altered to confer the desired stability. The method may be applied to any enzyme which is cleaved in the presence of chlorine and is particularly applicable to alkaline proteases.

SUMMARY OF THE INVENTION

The invention provides a method of identifying a site of enzyme cleavage in the presence of hypochlorite; a method of increasing the stability of an enzyme to cleavage at tryptophan in the presence of hypochlorite; hypochlorite stable enzymes which have been modified at the tryptophan cleavage site; and a detergent composition including an alkaline protease containing a modified tryptophan residue. The invention is applicable to all enzymes cleaved at tryptophan in the presence of hypochlorite, and is particularly applicable to serine proteases such as alkaline proteases.

The method of identifying a site of enzyme cleavage in the presence of hypochlorite, includes the steps of:

a. adding hypochlorite to an aqueous solution of the enzyme to produce peptide fragments;
b. precipitating the fragments and any uncleaved enzyme;
c. separating the peptide fragments under conditions which prevent reactivation of the enzyme; and
d. identifying terminal amino acids of the separated fragments.

An enzyme stable against cleavage at tryptophan in the presence of hypochlorite can be produced by modification of the tryptophan cleaved. Modification can be accomplished chemically or genetically. Genetically, tryptophan may be deleted and an amino acid which is not cleaved in the presence of hypochlorite may be inserted. Genetic manipulation by site directed mutagenesis is preferred to produce an altered enzyme containing a tyrosine or phenylalanine to replace tryptophan at identified cleavage sites.

The invention is especially useful to produce detergent alkaline proteases, altered at a tryptophan cleavage site between amino acid 95 and 125, by replacing Trp with a tyrosine or phenylalanine. Such detergents may then be used in conjunction with bleaches such as Clorox ®.

DEFINITIONS

Alkaline proteases

Alkaline proteases are serine proteases like the subtilisins with broad specificity for peptide bond hydrolysis. These enzymes are stable and active in the pH range 6 to 12. MILEZYME ®, and SAVINASE ® are two of the alkaline proteases sold commercially as detergent additives. SAVINASE is available from Novo, 59 Danbury Rd., Wilton, Conn., and has the N-terminal sequence shown below:

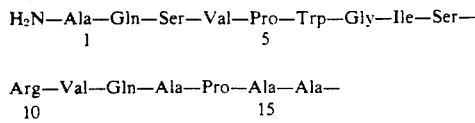

Arg—Val—Gln—Ala—Pro—Ala—Ala—
10                    15

APL

Figure 1:
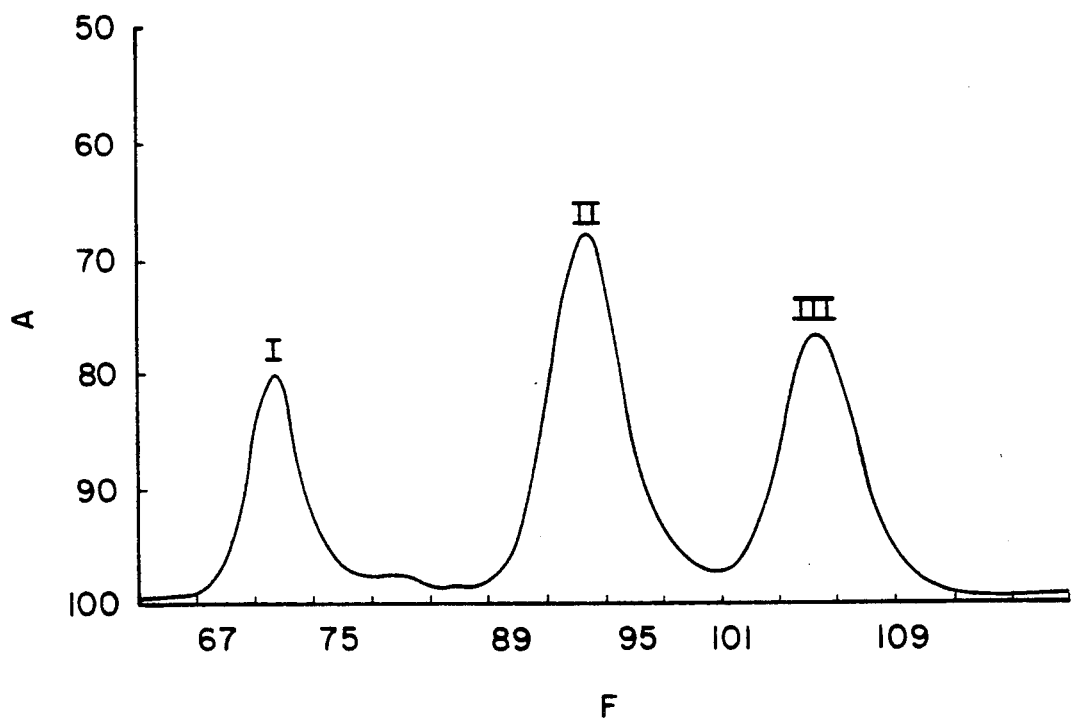
FIG. 1 shows the pattern of elution of hypochlorite-induced fragments fractionated on a Sephadex G75 superfine gel filtration column. The fraction number, F, is shown on the abscissa and the absorbance, A, is shown on the ordinate. The absorbance peaks are labeled I, II and III, corresponding to uncleaved protein having a molecular weight of approximately 28,000 Daltons (Da); a fragment having a molecular weight of approximately 18,000 Daltons; and a fragment having a molecular weight of approximately 10,000 Daltons, respectively. The experiment from which these data were generated is described in detail in Example 1.

APL is an alkaline protease synthesized by *Bacillus licheniformis* and sold by Miles Inc., Elkhart, Ind. 46515 as MILEZYME ®. The complete amino acid sequence of APL has been published, J. Biol. Chem., Vol. 243, No. 9, 2184-2191, 1968. The protein sequence and standard numbering system used generally with alkaline proteases is shown in FIG. 1.

APL Gene

The APL gene is the gene encoding the alkaline protease from *B. licheniformis.*

Modification

Modification of tryptophan cleavage site is defined to include chemical modification to produce an enzyme insensitive to oxidative cleavage at tryptophan, as well as genetic manipulation to delete tryptophan (Trp) at the cleavage site or to change Trp to another amino acid.

DETAILED DESCRIPTION OF THE PREFERRED EMBODIMENT OF THE INVENTION

Enzymes such as lipases, proteases, and amylases are used for many applications and have great commercial significance. These enzymes may come in contact with hypochlorite during their use and can be improved by method of the invention.

While it is known that enzymes, in particular alkaline proteases, are inactivated in the presence of hypochlorite, it is generally believed that such inactivation is due to oxidation of amino acids such as methionine (Stauffer, C. E. et al., 1969, J. Biol. Chem., 244, 5333-5338). Therefore previous work has focused on the possible oxidation of methionine. Methionine is oxidized to methionine sulfoxide or methionine sulfone but the peptide backbone is not cleaved. EP 0130756, while suggesting that replacement or deletion of one or more methionine, tryptophan, cysteine or lysine might improve oxidative stability, disclosed examples of replacement of methionine to improve oxidative stability.

However, by the method of this invention, it was found that enzymes are cleaved in the presence of hypochlorite to produce discrete polypeptide fragments. Such cleavage is associated with inactivation of the enzyme. Indeed it was found for APL that while methionine oxidation did occur, the enzyme remained active until cleaved. By processing the bleach inactivated enzyme immediately to prevent further cleavage of the polypeptide fragments by general proteolytic degradation, it is possible to isolate and separate the fragments and to identify the amino acid cleaved and the location of the cleavage site in the polypeptide backbone.

After identification and location of the cleaved amino acid, an altered protein can be produced by modification of the cleaved amino acid. Modification can be accomplished by chemical means or preferably by genetic manipulation to delete or replace the susceptible amino acid residue.

The existence of specific cleavage points at a tryptophan residue has been proven by the method of the invention for APL, SAVINASE and a non-protease enzyme, lysozyme. It was shown that the formation of polypeptide fragments and inactivation of the proteases were concomitant and occurred at approximately the same concentration of hypochlorite.

The method of identifying a bleach sensitive site of an enzyme begins with contacting the enzyme with hypochlorite. Upon fragmentation, the polypeptide fragments become more susceptible to cleavage by uncleaved enzyme, if the enzyme is an active protease. Any uncleaved protease must be inactivated to prevent degradation of the fragments. Inactivation can be accomplished by adding trichloroacetic acid (TCA) to produce a final concentration of TCA of from 5 to 50% by weight, preferably about 10%. The peptide fragments are separated under conditions which prevent reactivation of the protease. One method comprises collecting the precipitated protein and polypeptide fragments by centrifugation and resuspending the pellet in a solution of formic acid. The intact enzyme and polypeptide fragments thus obtained can be separated by fractionation on a molecular sieve column. However, other methods of separation such as gel electrophoresis, high pressure liquid chromatography, starch gel electrophoresis or paper chromatography, which are well known in the art, can also be used. The method described generally above is illustrated in detail in Example 1 as applied to APL.

Once the hypochlorite-generated fragments are separated, the sequence of these peptides at their amino termini can be determined. For example, sequences of the APL fragments were then compared to that of the intact protein from *B. licheniformis*, since this sequence had been published, and the position of these segments in the enzyme were determined. For APL, the fragments observed were generated by cleavage of the protein at the amino acid tryptophan at position 113.

The method of identification of cleavage fragments was followed for a second alkaline protease, SAVINASE, and for lysozyme. Separation and sequencing of the fragments indicated that enzyme cleavage in the presence of hypochlorite takes place at a tryptophan residue in all three cases and is believed to be a common cleavage site for all enzymes. A tryptophan cleavage site is shown below:

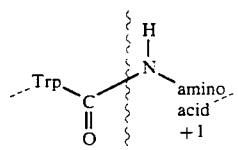

From the fragmentation pattern it is possible to deduce how many cleavage sites are present and the location of such sites.

The experimentation performed on SAVINASE generated a more complex peptide fragment pattern than that seen with APL. Nevertheless from the analysis of the hypochlorite-generated fragments it is apparent that three tryptophan residues are present in the molecule: at amino acid 6; between 90 and 125, most probably between 105 and 120; and between residue 200 and 250, probably between residue 225 and 250. One tryptophan cleavage site, between positions 90 and 125, overlaps with the tryptophan site for APL. Since alkaline proteases exhibit a high degree of homology with each other, it is believed that this Trp location is a common cleavage site for alkaline proteases.

The analysis of hypochlorite-generated fragments by such a protocol can be performed for any enzyme having a sensitivity to oxidation arising from the attack of tryptophan by bleach. The method is particularly applicable to proteases and is particularly important for alkaline proteases used in detergent formulations. Manual or computer aided comparison of protein sequences can be used to identify the cleavage site.

While the problem of cleavage and inactivation in the presence of hypochlorite is a general problem with enzymes, in particular, the many proteases used industrially, the invention will be illustrated with details of the preferred embodiment with alkaline proteases.

Alkaline proteases are not stable in the presence of hypochlorite, a strong oxidizing agent. These proteases are usually inactivated by very low concentrations of hypochlorite (as little as 200 $\mu$M, or less than 0.1 Cup, in a standard 64 L washer tub of water.) This concentration is much below the desired use level for such bleach, e.g. $\frac{1}{2}$ Cup of chlorine bleach is often used in a washer tub of water which approximates 3 mM hypochlorite depending on the volume of the water used.

A common cleavage site Trp between 90 and 125 has been identified and for alkaline proteases, this Trp residue is preferably changed to a tyrosine or phenylalanine by site directed mutagenesis to provide an improved hypochlorite stable alkaline protease.

Cloning of the Gene for Mutagenesis of the Tryptophan Residue in the Protein

The gene encoding an enzyme must be cloned in order to modify the product of the gene by genetic manipulation. Specifically, an enzyme displaying a resistance to hypochlorite-induced polypeptide chain cleavage can be most effectively produced by:
1. Cloning a gene comprising a DNA sequence capable of encoding the enzyme or a segment thereof containing the hypochlorite cleaved tryptophan;
2. changing a DNA sequence within the cloned gene or segment thereof to produce a variant of the gene (mutant) whose predicted product would not contain tryptophan residues at the hypochlorite sensitive site;
3. expression of the altered enzyme either from its own transcription and translation signals or following the replacement of these signals with more advantageous DNA elements;
4. purification of the native and altered enzyme followed by demonstration of the resistance of the altered enzyme to oxidative polypeptide chain cleavage.

Thus, it is expedient either to clone the entire APL gene encoding the enzyme or clone as complete a segment of the gene as can be readily obtained.

Identification of the DNA segment to be cloned can be done by Southern hybridization of digested chromosomal DNA from the organism producing the desired enzyme to probe sequences designed to bind to the gene encoding the enzyme. Such probe sequences can be obtained from analysis of a published sequence of the gene as was done for the APL gene. However, when the sequence of the desired gene is not available, probe sequences can be obtained by the process of reverse translation of protein sequences obtained from the desired enzyme such as those determined for identification of the hypochlorite cleavage sites in the enzyme. One skilled in the art can analyze the many potential probe sequences that are generated in such a way to determine those most likely to identify only the desired gene in the presence of the other DNA sequences present within the bacterial chromosome.

The DNA fragment encoding the desired gene can then be enriched by the process of gel isolation and can subsequently be physically fused to an easily identified DNA segment known in the art as a vector by the process known as DNA ligation. The fragment-vector construct, known as a clone, can be introduced into a bacterial host by the process of transformation and the desired clone can be identified by hybridization of the DNA from the transformed bacteria to the DNA probe described above. The DNA sequence of the clone can then be obtained by techniques commonly used in the art in order to confirm that the proper DNA segment has been cloned and to identify restriction sites and obtain sequence information necessary for subsequent alteration of the gene encoding the protein. It is understood that other methods can be used to produce the desired clone such as techniques relying on the purification of the RNA transcription product of the gene or those which use immunochemical methods for the identification of desired clones. Those sufficiently skilled in the art would be familiar with these various techniques.

Mutagenesis of the Cloned Gene Segment

Mutagenesis of the cloned genes for the purpose of removal of offending tryptophan (Trp) residues can then be performed following subcloning of the gene into a phage vector known as M13. Site directed mutagenesis by the procedures described by Zoller, et al, DNA, Vol. 3, No. 6, 1984 can then be performed to alter the regions of the gene encoding the Trp residues. Selection of the residues to be used to replace the offending tryptophans can be determined by computer modeling of the gene if the tertiary structure of the protein is known. However, in general such information would not be known. In such cases it would be best to attempt to replace the Trp residues with amino acids which have a similar shape (planar) and similar chemical properties (aromatic) since such replacements would have the least chance of causing major alterations in the structure of the protein. With this in mind, the first alterations to make would be mutation of the Trp residues to either tyrosine (Tyr) or phenylalanine (Phe) residues, since these amino acids fulfill the requirements listed above and are more resistant to oxidation than is tryptophan. Although the technique of site directed mutagenesis can be employed as described, other mutagenic protocols such as cassette mutagenesis and localized random mutagenesis can also be used. An alternative to this approach would be to modify the tryptophan chemically so that such residue would be insensitive to attack by hypochlorite.

Expression of the Wild Type and Altered Protease Genes

If the intact gene is cloned, this gene segment can be fused to a vector capable of propagation in a host organism. Upon cloning of the gene in a host species such as *E. coli* expression of the cloned DNA segment may fortuitously occur. If expression of the isolated DNA segment is not observed, as measured by detection of the enzyme in cultures of the host carrying the recombinant plasmid, the gene can be transferred to another host, such as *B. subtilis*, where production of the enzyme would be more likely. If the enzyme is still not produced, the DNA elements responsible for transcription and translation initiation on the gene could be exchanged for those which operate in the desired host species.

If an incomplete segment of the gene is isolated, as judged by the DNA sequence of the cloned DNA, the data obtained can in turn be used to isolate the missing gene segment. The two segments encoding the gene can then be fused to produce an intact copy of the gene. Alternatively, the missing DNA sequence can be synthesized if either the actual DNA or protein sequence of the absent region is known. One can then provide this partial gene with transcription and translation initiation regions for expression of the protein in the host organism of choice. Work would then proceed as described earlier in this section.

If either the essential protein sequence of the enzyme or the DNA sequence of the gene has been obtained, the entire gene can be produced synthetically and no DNA isolation from the natural host would be needed. In addition a wide variety of vectors allowing plasmid maintenance are available and many DNA segments which allow the transcription and translation of foreign genes are known. Once expression of the native enzyme is observed, the natural gene can be replaced with the mutated gene for expression of the altered protein.

Determination of the Hypochlorite Sensitivity of the Various Enzymatic Forms Expressed Unfortunately, crude enzyme preparations obtained from various host species contain components which can mask the affect of hypochlorite on the enzyme of interest. It is therefore essential to remove contaminants which inactivate hypochlorite such as $\beta$-mercaptoethanol or amine buffers such as TRIS before an accurate measurement of the effect of hypochlorite on these enzymes can be made.

The following specific examples of APL, SAVINASE and lysozyme further illustrate the invention but are not to be construed as limiting. This invention can be applied to any enzyme which is cleaved at tryptophan in the presence of hypochlorite and to proteases and alkaline proteases of commercial use in particular.

SOURCES AND ABBREVIATIONS

VIRUSES

1. M13mp18 and M13mp19—*E. coli* phage available from New England Biolabs, 32 Tozer Road, Beverly, Mass., 01915.
2. M13APL—an *E. coli* phage deposited with the ATCC acession number 40438, carrying a segment of APL DNA useful herein.

BACTERIAL STRAINS

1. JM105—An *E. coli* strain available from United States Biochemical Corp. P.O. Box 22400, Cleveland, Ohio, 44122.
2. GX4926 deposited at USDA Northern Regional Research Laboratory, Peoria, Ill., with accession number B-15811 and described in WO 86/01825.

CHEMICALS

1. X-Gal—5-Bromo-4-chloro-3-indolyl-$\beta$-D-galactoside available from United States Biochemical Corp.
2. IPTG—Isopropyl-$\beta$-D-thiogalactopyranoside available from United States Biochemical Corp.
3. SDS—sodium dodecyl sulfate
4. BSA—bovine serum albumin

PLASMIDS 1. pRW33—A plasmid carrying the penPC gene (FEBS letters, vol. 161, No. 2, pgs. 195-200)
2. pCPP-4—A *B. subtilis*—*E. coli* shuttle vector ATCC No. 37277

All concentration percentages (%) are weight/weight unless otherwise specified.

EXAMPLES

EXAMPLE 1

APL

Hypochlorite Action on APL

Cleavage of APL was achieved by treatment with chlorine bleach at a final concentration of approximately 3 mM. TCA was then added to a concentration of 10% and the resulting protein precipitate was collected by centrifugation at $6000 \times g$ for 15 minutes. The protein pellet was resuspended in a small amount of 70% formic acid (1 to 3 mL per 20 mg protein). The solution was shown to contain some undigested protein and two new polypeptides of 18,000 and 10,000 daltons which were generated by cleavage of the intact enzyme. These species were separated by fractionation on a 2.5×90 cm column of Sephadex G75 Superfine equilibrated with 9% formic acid. Fractions (1.8 mL) of the column eluate were collected. The elution of the polypeptides was monitored with a flow cell UV detector (FIG. 1), and fractions containing the various eluted fragments were pooled and lyophylized.

Cleavage Site Identification

Amino acid sequencing was performed using Applied Biosystems Moedl 477A/120A Sequencer Analyzer System. Sequence analysis of the 10,000 Da peptide (Pool III) revealed that this fragment corresponded to the N-terminus of APL. When the 18,000 Da fragment (Pool II) was subjected to Edman degradation, it yielded a sequence which matched the published sequence of the protein starting with amino acid 114 of APL (Table 1). Thus, this method proved that bleach treatment of APL resulted in the cleavage of the molecule at Trp 113, resulting in the generation of a 18,000 Da peptide (residues 114 to 274 of APL), and a 10,000 Da fragment containing the amino terminal portion of the protein.

Cloning of a Portion of the Alkaline Protease Gene from *B. licheniformis*

A segment of the gene encoding the alkaline protease from *B. licheniformis* was cloned in order to modify the gene product to produce a bleach stable form. A DNA fragment carrying a segment of the gene containing the offending Trp residue was identified by Southern hybridization of the chromosomal DNA from a *B. licheniformis* to a probe homologous to a selected region of APL (shown specifically later). Chromosomal DNA (10 μg) was digested with various restriction endonucleases, and the resulting DNA fragments were fractionated by electrophoresis using a 0.8% agarose gel and TBE buffer (10.8 g Tris, 5.5 g boric acid, 4 mL of 0.05M EDTA pH 8.0) following addition of 10×TBE sample buffer (formulation consisting of 0.06 g xylene cyanol, 0.06 g bromophenolblue in 10 mL of 50% glycerol). A sample of phage lambda DNA digested with restriction endonuclease HindIII was included on the gel to serve as a size standard. The DNA was electrophoresed overnight at low voltage (40 V) on a large agarose gel (6.5×6.0 inches). At this voltage, the bromophenolblue dye had migrated approximately 5 inches through the gel. The gel was stained by soaking in ethidium bromide (0.01 mg/mL) and photographed using short wave UV light. The separated DNA fragments were transferred to a nitrocellulose membrane by the method described in "Molecular Cloning: a Laboratory Manual", T. Maniatis, E. F. Fritsch, and J. Sambrook, 1982, Cold Spring Harbor Laboratory, pgs 382–386. The nitrocellulose filters were then prehybridized at 65° C. for three hours in 20 mL of 0.25% nonfat instant dry milk in 2× Saline Sodium Citrate (SSC). (20× SSC is made by dissolving 175.3 g of NaCl and 88.2 g of sodium citrate in 800 mL of water. The pH of the solution adjusted to 7.0 and the solution is diluted to the desired strength before use without subsequent pH adjustment (unless specified)). Following prehybridization, a $^{32}P$ labeled probe described below was added to a final concentration of 2.5×10$^6$ cpm/mL and the hybridization reaction was conducted overnight at room temperature on a rotary shaker. The membrane was washed three times in 20 mL of 2×SSC, 0.1% SDS at 50° C. for 10 minutes, dried in air and placed on an X-ray film. After several days, the exposed film was developed and the gel was shown to have only one hybridizing band in each lane of the fractionated, restricted DNA. The result confirmed that, at the proper stringency, only one DNA segment in *B. licheniformis* hybridized to the probe sequence used. The mobilities of the hybridizing bands were then compared to the fragments from the standard and the molecular weights of the hybridizing fragments were estimated. It was found that the DNA fragment which carries the hybridizing region of the APL gene following restriction of the DNA with endonuclease HindIII was approximately 2.1 kb. The fragment was cloned to obtain a copy of APL gene.

The probes used to identify the APL gene were synthesized by using the phosphoramidite chemistry (Beaucage, S. L., Caruther, M. H. (1980) Tetrahedron Letters, Vol. 22, pp 1859–1862 on the Applied Bio-systems DNA Synthesizer, Model 380A, Foster City, Calif.) The synthesized oligonucleotides were purified by preparative polyacrylamide gel electrophoresis. The sequence of the probes used were:

5'
AACGGAACGTCAATGGCTTCTCCT-
CACGTTGCCGGAGC and

5'
CTTAGAAAGAAT-
CAAAGCTGCTGCTCCGGCAACGTG

These probes were labeled with radioactively labeled deoxynucleotides as is well known in the art.

The cloning of the 2.1 kb fragment which carried a segment of the APL gene was initiated by digestion of chromosomal DNA (150 μg) from the *B. licheniformis* strain tested above was digested with endonuclease HindIII (450 U) in a buffer composed of 100 mM NaCl, 50 mM Tris-HCL pH 7.5, 10 mM MgCl$_2$, and 1 mM dithiothreitol, in a volume of approximately 450 μL. The reaction mixture was incubated for several hours at 37° C. and loaded onto a preparative 0.8% agarose gel. Lambda DNA digested with this endonuclease was again included on the gel as a size standard. The gel was run overnight at 40 V, and the DNA bands were stained with ethidium bromide as described above. The DNA was visualized under short wave UV light, and a slit was made in the gel through the lanes containing the digested chromosomal DNA across from the 2.0 kb DNA fragment present in the standard. The gel was returned to the electrophoresis chamber and a strip of DEAE cellulose was inserted into the slit in the gel. Current was applied to the gel until the 2.2 kb DNA fragment of the standard migrated to the position of the slit. The DEAE strip, now containing the DNA fragments ranging in size between 2.0 and 2.2 kb was removed from the gel and placed in a 1.5 mL Eppendorf tube. One milliliter of TE buffer (10 mM Tris-HCl, pH 7.5, 1 mM EDTA) was added to the tube and the contents of the tube were mixed by vortexing until the paper was pulverized. The microfuge tube was spun 5 minutes and the supernatant was discarded. The pellet was suspended in 1.0 mL of TE, spun 5 minutes in a microfuge and the supernatant was again discarded. The pellet was resuspended in 450 μL of 1.5M NaCl containing 40 mM arginine free base and the tube was shaken well for 10 minutes. The tube was centrifuged in a microfuge for five minutes and the supernatant, containing eluted DNA fragments, was placed in a fresh 1.5 mL Eppendorf centrifuge tube.

A solution (900 µL) of 95% ethanol was added to the tube, the mixture was chilled at −70° C. for 15 minutes and spun in a microfuge as described above. The supernatant was discarded, the pellet was rinsed once in 70% ethanol and respun as above. The pellet was dried under vacuum and the DNA was resuspended in 20 µL of water.

Approximately 200 ng of M13mp19 was digested with HindIII endonuclease under the conditions described above except the final reaction volume was 50 µL. The digested DNA reaction mixture, to which 50 µL of water was added, was extracted with 100 µL of chloroform-phenol, and the aqueous layer was transferred to a 1.5 mL Eppendorf tube. A solution of 95% ethanol (900 µL) was added to the tube and the tube was chilled at −70° C. for 15 minutes. The tube was centrifuged in a microfuge 5 minutes, the supernatant was discarded and the DNA pellet was dried under vacuum. The following solutions were added to the dried DNA: 1 µL of 10×ligase buffer (0.5M Tris-HCl (pH 7.5), 0.1M MgCl$_2$, 0.1M dithiothreitol, 10 mM spermidine, 10 mM dATP, and 1 mg/mL BSA), 2 µL of the isolated fragments, 6 µL of water and 1 µL of T4 DNA ligase. The reaction mix was incubated for 1 hour at room temperature and the ligation reaction was used to transfect competent E. coli JM105 (competent cells produced by the procedure described in Maniatis et al, cited previously, pgs. 250-251, steps 1-5). Ten separate incubations, each using 1 µL of the ligation mixture, were performed each using one tube of competent cells. The competent cells and the ligated DNA were incubated 1 hour at 4° C. and the cells were then placed in a 42° C. water bath for 2 minutes. One milliliter of L-broth was added to each transfection and the transfectants were then divided into six aliquots in sterile tubes. One drop of an overnight culture of JM105 was added to each tube. Three milliliters of top agar were then placed into each tube and the contents were gently mixed and plated onto L-agar plates spread with 100 µL each of 10 mg/mL X-Gal in dimethylformamide, and 100 mM IPTG. (Note that it is important to let these spread solutions dry before using the plates). The plates, incubated at 37° C. overnight, were found to contain blue plaques and clear plaques. The blue plaques indicated regions where cells carrying the M13mp19 vector devoid of insert DNA had grown. Clear plaques indicated regions where cells carrying the M13mp19 vector containing a DNA insert had grown. In all, three series of ligations and transfections were performed in order to obtain a pool of approximately 600 clones containing insert DNA. When few clear plaques were present on a transformant plate, the clear plaques were individually picked and placed in a sterile test tube along with 15 µL of an overnight culture of JM105 and 1.5 mL of L-broth. The tubes were incubated for six hours at 37° C. and 200 rpm, and the contents of the tubes were transferred to a 1.5 mL Eppendorf tubes. After centrifugation, one microliter of each supernatant was spotted on a nitrocellulose filter. The rest of the supernatants were discarded and the cell pellets were frozen. The filter was air dried and baked at 80° C. for 30 minutes, and then hybridized as described for Southern blots of chromosomal DNA.

When the plates displayed many clear plaques, the plaques were lifted onto nitrocellulose. The discs were baked at 80° C. for 60 minutes under vacuum to immobilize the DNA. The hybridization with synthetic probes was then carried out as described for nitrocellulose blots of agarose gels described above. Two plaques were shown to hybridize strongly to the labeled probe, one plaque originating from the spotted cell supernatants, and the other from a a plaque directly lifted from a plate. The plaque present on the plate was picked as an agar plug and propagated as described above for those picked from plates containing few clones. The cell pellet from both of these clone propagations were used to produce double stranded phage DNA by a protocol slightly modified from that of Birnboim and Doly, (Nucleic Acids Research, Vol. 7, p1513, 1979), and 1 µL samples of these DNAs were used to transfect fresh, competent JM105. Both of these transfections produced many clear plaques which displayed strong hybridization upon plaque lifting and reprobing as described above. Three strongly hybridizing plaques from each of the resulting progeny phage were picked and propagated in liquid by placing an agar plug containing the plaque in 1.5 mL of medium with 15 µL of JM105 from an overnight culture, and incubating the resulting mixture at 37° C. and 200 rpm for six hours. The supernatants from these cultures were saved and used for the preparation of template DNA. The DNA was sequenced by the techniques of Sanger et al, Proc. Natl. Acad. Sci., USA, Vol. 74, pp5463-5467, 1977. However, internal DNA primer segments, made to match the published sequence of the APL gene were used in addition to the universal primer in order to obtain the sequence of the entire APL coding region present in these phage more rapidly. The derived sequence was shown to contain an open reading frame which, when translated, exactly matched the published protein sequence of APL from amino acid 55 of the mature protein through the carboxy-terminus of the protein.

The cloned region of the APL gene contains the Trp residue shown to be sensitive to hypochlorite-induced polypeptide chain cleavage, and as such can be used for modification of the gene at this location to produce a protein which would be resistant to cleavage.

The data reported above verify that the segment of the APL gene encoding the mature protein sequence from amino acid 55 through the carboxy terminus of the protein has been cloned.

Subcloning of the APL Gene and Site Directed Mutagenesis of the Coding Region of the Gene The coding region of APL is flanked by a HindIII and XmnI site. These sites were used to subclone the desired DNA fragment into M13mp19 for the purpose of site directed mutagenesis, as described below.

Approximately 200 ng of the original clone DNA was digested with HindIII and XmnI and the resulting DNA fragments were fractionated on a 0.8% agarose gel. The fragment of approximately 750 base pairs was gel isolated as described earlier for chromosomal DNA. The isolated DNA fragment was mixed with approximately 200 ng of M13mp19 digested with HindIII and HincII. The DNAs were ligated and used to transfect competent JM105 as described above and several of the resulting clear plaques were used to obtain double stranded DNA as before. Restriction digestion and subsequent DNA sequence analysis performed as before confirmed that these clones contained the desired DNA segment necessary for site directed mutagenesis for modification of the gene in order to replace the trp113 residue in the encoded product. This clone was given the name M13APL. Template DNA was prepared from these clones as was done for sequencing of the original clone of the gene, and this DNA was used to perform site directed mutagenesis. The mutagenesis was performed essentially as described in Zoller and Smith, DNA, Vol. 3, No. 6, 1984. The mutagenic primers used were:

a) for alteration of tryptophan to phenylalanine,

GAA TCG AGT TCG CGA CAA C;

b) and for alteration of tryptophan to tyrosine,

GAA TCG AGT ACG CGA CAA C

These mutagenic primers were used in conjunction with a primer complementary to the M13 DNA to improve the efficiency of mutagenesis as is well known in the art. The sequence of this segment was:

GAG AGA TCT ACA AAG GCT ACT

The plaques resulting from the mutagenesis protocol were screened with the mutagenic primers described above which had been radiochemically labeled. Those plaques which might contain the desired mutations, based on their stringency of hybridization, were propagated and sequenced as described previously using the primer listed below:

described earlier referred to herein as M13 APL, deposited as lyophilized sterile bacteriophage with the ATCC, accession numbers 40438. It is convenient at this point to provide the desired clone with restriction endonuclease sites to make the addition easier.

In order to obtain DNA of the M13 APL clone for addition of the oligonucleotide segments, the M13 APL clone was retransformed into competent JM105 as described above and one of the resulting plaques was propagated in a 25 mL liquid culture as described above. From the cells obtained from this culture, double strand phage DNA was isolated by scaling up the procedure described above and dissolving the DNA in 1 mL of water. A 50 µL portion of this DNA was digested with BgII and HindIII in a 500 µL total reaction volume using 50 µL of 10× high salt restriction buffer obtained from Boehringer Mannheim, Indianapolis, Ind. The digested DNA was extracted with 500 µL of phenol: chloroform, and the aqueous layer was mixed with 50 µL of 3M sodium acetate, pH 5, and 1.5 mL of 95% ethanol. The solution was chilled at −20° C. for 30 minutes and centrifuged in a microfuge at 13,000 rpm for 30 minutes. The supernatant was removed by decantation and the pellet, which contained the DNA, was dried under vacuum. The DNA was then dissolved in 300 µL of distilled water.

The oligonucleotide segments JS96 and JS97 were dissolved to a concentration of 1 mg/mL in distilled water and 2 µg samples of each of these DNAs were then placed into 36 µL of water and incubated 20 minutes at 4° C. (Oligonucleotide segments used are shown in TABLE 1).

TABLE 1

JS 96:
5'-AGC CGG ATC CGA TAT CCG CGG CGC AAA TTT CCG GAC
TTG AAC GTA GTC GGC GGA GCA AGC TTT GTG GCT GGC GA-3'

JS 97:
5'-AGC TTC GCC AGC CAC AAA GCT TGC TCC GCC GAC TAC
GTT CAA GTC CGG AAA TTT GCG CCG CGG ATA TCG GAT CCG
GCT GAA-3'

JS 98:
5'-GGC GCA AAC CGT TCC TTA CGG CAT TCC TCT CAT TAA
AGC GGA CAA AGT GCA GGC TCA AGG CTT TAA GGG AGC GAA
TGT AAA AGT AGC CGT CCT GGA TAC AGG AAT CCA AGC TTC
TCA T-3'

JS 99:
5'-CCG GAT GAG AAG CTT GGA TTC CTG TAT CCA GGA CGG
CTA CTT TTA CAT TCG CTC CCT TAA AGC CTT GAG CCG GCA
CTT TGT CCG CTT TAA TGA GAG GAA TGC CGT AAG GAA CGG
TTT GCG CCG C-3'

TGT ATT AGG CGT TGC GCC

From the DNA sequences of these clones, it was found that a large percentage of the selected clones carried the desired DNA alteration and that no other mutations were inserted into the clones in the region sequenced. From the mutants having the desired alteration, one carrying the phenylalanine alteration and one carrying the tyrosine alteration were selected for expression.

Expression of the Modified and Wild-Type APL Genes

Before the segment of the alkaline protease gene encoding APL can be used to express the full length mature protein, the DNA encoding the remaining amino acids comprising this segment of the protein must be added to the clone. This can be done by addition of synthetic DNA segments to the M13 subclone of APL The DNA solution was then incubated with polynucleotide kinase as described in Molecular Cloning: A laboratory manual, T. Maniatis, E. F. Fritsch, J. Sambrook. The phosphorylated DNA was added to 1 µL of the digested M13 APL, and these DNAs were ligated with T4 DNA ligase as described in the reference above. This DNA was used to transform competent JM105, and the transformed cells were spread onto L-agar plates and incubated at 37° C. overnight. Twenty of the resulting phage plaques were propagated in 1.5 mL liquid cultures as described above, and the cells were used for small scale DNA isolation. Small volumes (3 µL of 50 µL) of these DNA preparations were then digested separately with BamHI and PvuII in 50 µL reactions and the resulting DNA fragments were analyzed by agarose gel electrophoresis as described above. Seven of the DNAs obtained were judged to contain the proper insert as they displayed the expected fragment pattern with these two endonucleases. Five of these preparations were then selected for further study and digested with EcoRV, and the resulting DNA fragments were analyzed as described above. All of these preparations were shown to linearize with this enzyme, which was taken as confirmation that these clones were correct. The new construction was given the name M13APL96, and these plasmid preparations were used for construction of the next vector.

Figure 2:
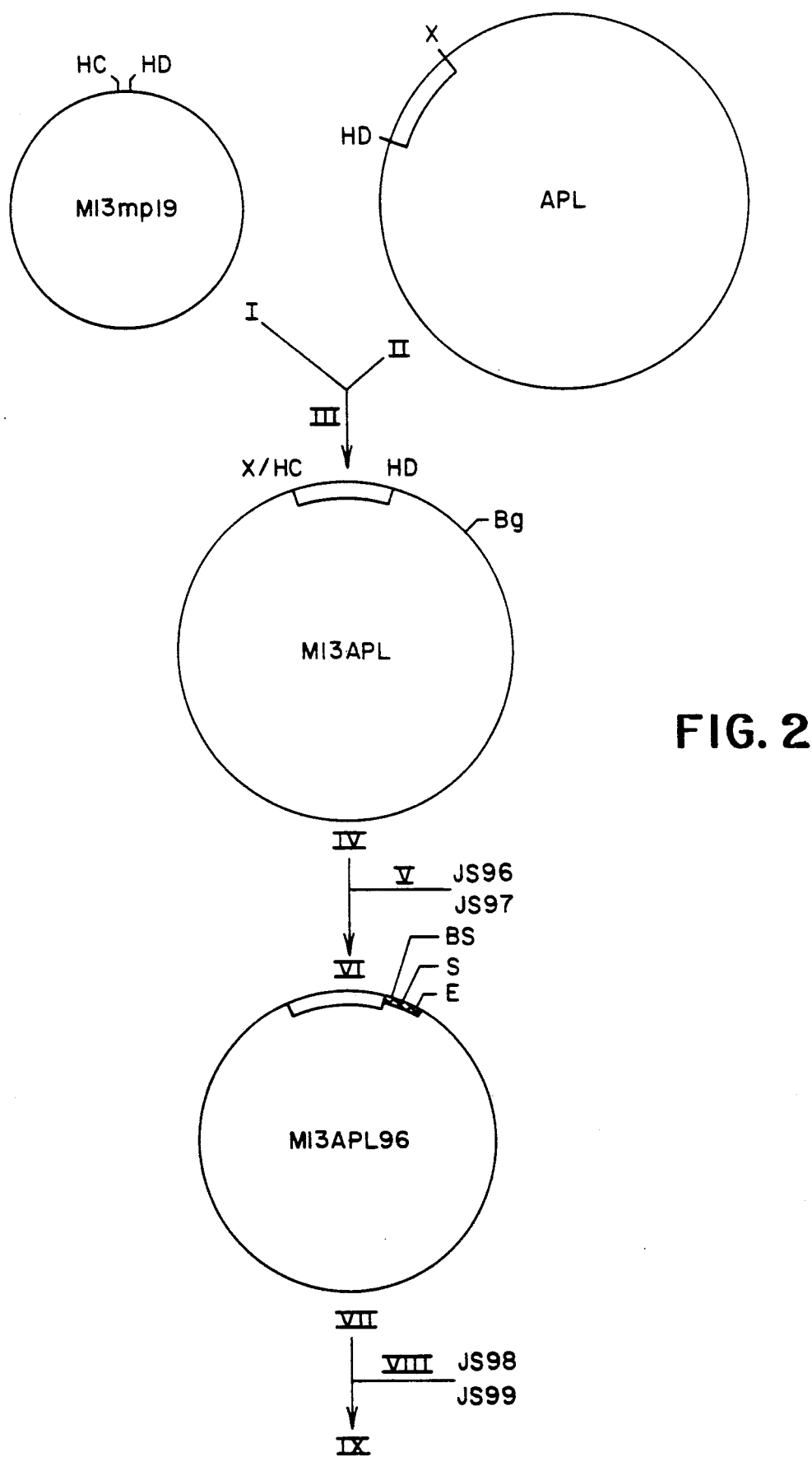
FIG. 2 and 2a show a diagram for the construction of an expression vector for an altered APL gene. Endonucleases are indicated as follows: HC is HincII, HD is HindIII, X is XmnI, Bg is BglI, BS is BspmII, S is SacII, E is EcoRV, C is ClaI, Bm is BamHI. The steps shown as Roman numerals correspond to: step I, digest M13mp19 with HincII and HindIII; step II, digest original APL clone and XmnI and HindIII and isolate fragments; step III, ligate DNA's of steps I and II to produce M13APL; step IV, digest M13APL with HindIII and BglI; step V, anneal JS96 and JS97, oligonucleotides shown in Table 1; step VI, ligate DNA's of steps IV and V to produce M13APL96; step VII, digest M13APL96 with BspmII and SacII; step VIII, anneal JS98 and JS99 oligonucleotide shown in Table 1; step IX, ligate DNA's of steps VII and VIII to produce M13APL98; step X, digest M13APL98 with EcoRV; step XI, digest pRW33 with ClaI and HindIII and blunt off fragments; step XII, ligate DNA's of steps X and XI to produce M13expAPL; step XIII, digest M13expAPL with BamHI; step XIV, digest pCPP-4 with BamHI; and step XV, ligate DNA's of steps XIII and XIV to produce pAPL-EXP, an expression vector.
Figure 2A:
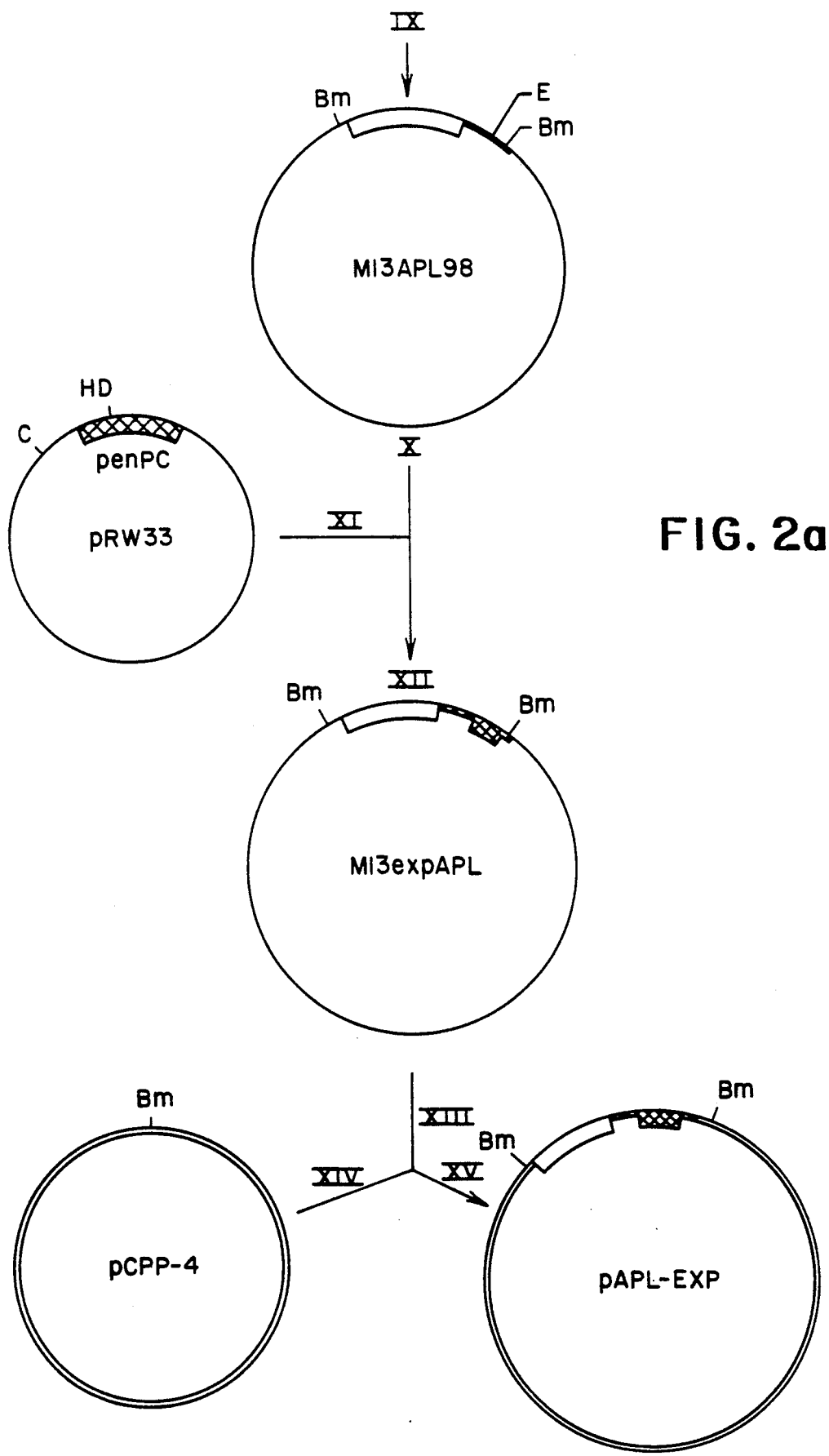

The second pair (JS98 and JS99) of oligonucleotides could then be added to the M13APL96 clone as described above except that the phage DNA would be digested with SacII and BspMII. The result of this construction could then be identified as M13APL98. However, this clone would be unable to express the desired protein as it contains neither the proper DNA signals needed for transcription and translation and secretion of the APL, nor those needed for replication in our host of choice for expression of the gene, $B$. $subtilis$. The gene can be provided with the proper DNA sequences needed for expression by fusion of the APL gene segment on the phage to sequences known to provide such signals in $B$. $subtilis$, such as those arising from the subtilisin gene or penPC (FEBS Letters, Vol. 161, No. 2., pgs 195-200) both of which encode proteins that are secreted. As will later become apparent, it is helpful to have the final product of expression of the gene secreted into the medium in which the host is propagated to simplify purification from other cellular products synthesized during cell growth. Therefore, it is advantageous to use DNA elements of the type defined above because they carry the proper secretion signals. The DNA sequences should be properly aligned so that the resulting chimeric gene encodes one reading frame that produces a hybrid product comprised of both proteins. This can be done, in the case of the penPC DNA sequence described above by digestion of plasmid pRW33 with endonucleases ClaI and HindIII and removal of the overhanging single stranded DNA segments by use of Mung-bean nuclease as described in Maniatis. These DNA fragments could be separated by agarose gel electrophoresis, and the fragment of approximately 750 base pairs which contains the desired fragment could be isolated from the gel as described above. Phage DNA from M13APL98 can be digested with endonuclease EcoRV and the resulting DNA can be extracted with phenol:chloroform as described above. The isolated DNA fragment from pRW33 and the digested M13APL98 are then ligated as described above and the DNA is used to transform competent JM105. Several of the resulting plaques are then propagated in liquid culture and the cells which result from these incubations are used for small scale DNA preparations. Aliquots from these preparations are analyzed using agarose gel electrophoresis and those showing an increased size compared to M13APL98 are studied further. These isolates are then sequenced in the region comprising the penPC-APL fusion site using internal DNA primers and Sanger dideoxy nucleotide sequencing as described for confirmation of the original APL clone. Those isolates which have the desired DNA sequence are then propagated in 25 mL cultures and DNA is isolated from them as described above. This new construct could then be named M13expAPL. The DNA could be digested with endonuclease BamHI in order to separate the chimeric gene from the phage DNA. The desired DNA could be isolated by agarose gel electrophoresis as described above, and could then be placed into a vector that can replicate in $B$. $subtilis$ and $E$. $coli$ as described below. A diagram of the protocol is shown in FIG. 2 and 2a.

Plasmid pCPP-4 (Band, L., Yansura, D. G. and Henner, D. J., Gene, Vol. 26, pp. 313-315, 1983, available as American Type Culture Collection acquisition No. 37277) could be digested with endonuclease BamHI, extracted with phenol:chloroform and precipitated with ethanol as described above. This DNA is ligated to the DNA fragment carrying the chimeric gene described above and the resulting DNA is used to transform competent $E$. $coli$. The transformation mixture is then plated on L-agar media containing neomycin, the resistant transformants that arise are propagated, and DNA is prepared from these isolates by protocols commonly employed by those skilled in the art. These DNAs are analysed by endonuclease digestion and agarose gel electrophoresis, and those which are comprised of the DNA fragment encoding the chimeric gene fused to pCPP-4 are identified on the basis of their restriction fragment pattern as would be apparent to those skilled in the art. Since there is no direct method for selection of the desired plasmid, it is important to analyze several of the transformants at this point. Transformants whose plasmid DNA displays the desired pattern are then retransformed into competent $E$. $coli$ as described above, and the resulting transformants are used to prepare cesium chloride purified DNA. These constructs can be identified as pAPL-EXP.

For ease of purification of the mutant and wild type forms of APL, it is advantageous to express the genes encoding these protein forms in a $B$. $subtilis$ host which does not produce a neutral or alkaline proteases usually made by these bacteria. Therefore, it is best to transfer the pAPL-EXP into one of several host strains carrying the desired mutations such as GX4926, deposited at USDA Northern Regional Research Laboratory, Peoria, Ill. with accession number B-15811 and described in WO 86/01825. However, protease-deficient $B$. $subtilis$ strains are not capable of taking up DNA by the usual protocols. Therefore, a protoplast transformation protocol such as described in Mol. Gen. Genet., 168, pp 111-115, by Chang, S., and Cohen, S. N. will be required for transfer of the plasmid. The transformants are selected for neomycin resistance, and the plasmids present in them are isolated by the small scale DNA isolation protocol described earlier. Those transformants whose plasmids display a restriction pattern identical to pAPL-EXP are grown in liquid medium containing neomycin.

During growth of the transformants, the optical density of the culture and the alkaline protease activity of the medium are monitored. When significant levels of activity are seen, the cells are removed from the medium by centrifugation. The APL protease is then purified from the medium by standard biochemical techniques.

In order to express the modified forms of the APL gene produced by site directed mutagenesis, it is necessary to insert the mutated DNA sequence into an expression vector. This can be done by digestion of the mutated M13 clones with endonucleases ScaI and SalI and gel isolation of the small fragment that would result from this digestion procedure. The clone M13expAPL is then also digested with these two endonucleases and the large DNA fragment is isolated as above. The two fragments are ligated together and used to transform competent JM105 cells. Several of the resulting plaques are propagated in liquid culture and this culture is then used to prepare template DNA for sequence confirmation of the clones. The mutant forms of the altered genes are then transferred to the pCPP-4 vector and transformed into a protease deficient *B. subtilis* host as described above. The resulting transformants are then propagated in liquid medium and the altered protein forms are purified as described above.

Demonstration that the Mutant Protein Forms are Resistant to Hypochlorite-Induced Polypeptide Chain Cleavage The purified wild-type and mutant proteases are then tested for their ability to resist hypochlorite-induced polypeptide chain cleavage. The proteins which are to be treated at a concentration ranging from 200 μg/mL to 10 mg/mL are first dialyzed against 200 mM sodium acetate buffer, pH 6.0, to remove any 5agents, such as TRIS, which might have been used during purification but would interfere with the analysis. A solution of sodium hypochlorite made in the same buffer is added to the protein in concentrations ranging from 100 μM to 3 mM and the solution is allowed to sit at room temperature for 5 minutes. A small sample is then removed for determination of the activity of the preparation and TCA is added to the remaining samples to a final concentration of 10%. The protein precipitate present in the TCA-treated samples is collected by centrifugation. The protein is then resuspended in an amount of SDS-sample buffer to give a suspension containing 2 μg of protein per μL and 20 μL samples of the solutions are fractionated on a 15% SDS-PAGE gel after heating at 95° C. for 5 minutes with vigorous agitation. It will be seen that while the wild-type enzyme cleaves in the presence of hypochlorite to produce the fragments described earlier, the mutant enzyme forms do not produce these fragments at the comparable hypochlorite concentration.

EXAMPLE 2

Hypochlorite Action on SAVINASE®

SAVINASE® was investigated to determine if the method of this invention could be used for analysis of an enzyme with an unreported amino acid sequence. Cleavage of Savinase (10 mg/mL) by hypochlorite was done as described for APL, and the protein precipitate was collected as described above. The protein pellet was resuspended in 70% formic acid and applied to a Sephadex® G75 Superfine column and fractionated as described for APL. Several protein pools were collected and two of these were subjected to automated sequence analysis. One of these pools, labeled pool II, gave a single sequence which did not match with the sequence which had been independently determined to be the amino terminus. Since the complete amino acid sequence was not known, a direct homology comparison could not be done as previously described. However it is known that alkaline proteases display a high degree of sequence similarity. This homology allows the derived sequences to be compared to that of APL and the location of the site of polypeptide chain cleavage in the Savinase sequence to be estimated. Such a comparison was done between APL and the derived sequence of the pool II fragment of SAVINASE using a computer program for homology search. The program used is present on the 1986 version of the IBI (International Biotechnologies, Inc., New Haven, Conn.) DNA/protein Sequence Analysis Systems software (disk 2, program D Search for Homology with a Subsequence.) The following parameters were used: the entire peptide sequence of APL was entered; no single residue was forced to be a perfect match; all matches greater than 25% were calculated. The analysis revealed that the sequence was similar to that of APL starting with residue 114 of the APL sequence. This suggested that protein cleavage took place in a region similar to that identified in APL and thus indicated that cleavage should have taken place between residue 90 and 129, probably between residues 105 and 119 of SAVINASE. The result was supported by the fact that the sequence of many of the alkaline proteases from several *Bacillus* species have a conserved tryptophan residue in this region of the protein. Computer analysis suggests that this protein would have tryptophan at this location and, by analogy to the situation seen for APL, that this Trp residue would create a site which would be sensitive to hypochlorite induced polypeptide chain cleavage.

Analysis of pool III revealed a double sequence where the predominant released residue could be identified in most cases. Comparison of these predicted sequences to the regions of SAVINASE, independently sequenced, revealed that this pool was a mixture of peptides having amino termini at residue 7 of the protein and a second peptide having an identical amino terminal sequence to that seen in pool II. It is important to note that amino terminal sequence analysis of the intact protein revealed a tryptophan residue 6 of the mature protein. Thus, these data again support the conclusion that hypochlorite cleaves protein at tryptophan. The data also suggest that this phenomenon is a general occurence and does not take place at Trp residues in a particular chemical environment. Identification of the pool II peptide sequence in pool III, which consisted of smaller protein fragments, indicated that another peptide cleavage near the carboxy terminus of SAVINASE must have taken place which removed approximately 20 to 40 amino acids from the protein. The analysis thus indicated that hypochlorite treatment of SAVINASE resulted in cleavage at residue 6; in a region between residue 90 and 125, probably between residues 105 and 119 of the protein; and, in a region near the carboxy terminus of the protein, probably between residues 235 and 250 of the enzyme.

EXAMPLE 3

Hypochlorite Action on Lysozyme

To verify that cleavage of proteins by hypochlorite takes place at tryptophan residues not only in proteases such as alkaline proteases but also in other classes of enzymes, the effect of the addition of hypochlorite on lysozyme was studied. Lysozyme was chosen for several reasons: it is a well studied protein which has a known amino acid sequence; the sequence of this protein contains several tryptophan residues which would be expected to be cleaved during hypochlorite treatment; the protein is commercially available; finally the protein contains other amino acid residues which are very sensitive to oxidation, such as methionine and cysteine.

Samples of 20 mg of lysozyme in 100 mM sodium acetate buffer, pH 5.5, were treated with 200 μM, or 400

μM hypochlorite, and trichloroacetic acid (TCA) was added to the resulting solutions to a final concentration of 10% TCA. A control sample was not exposed to hypochlorite. The precipitated protein samples were resuspended in 5 mL of 0.1% trifluoroacetic acid (TFA) and applied to a 2.5×100 CM column of Sephadex G50 Superfine equilibrated in 0.1% TFA. Elution of protein from the column was followed as described for APL and various protein pools were subjected to automated amino acid sequence determination as described above.

Only one major protein peak could be shown to elute from the untreated pool. This protein displayed only the sequence of the amino terminus of lysozyme when analysed. These data indicate that the protocols used do not in themselves lead to polypeptide chain cleavage and that the protein used was not internally cleaved.

The material treated with 200 μM hypochlorite displayed several different protein pools and analysis of one of these pools gave a double amino acid sequence. To determine the origin of these sequences, a computer homology search was carried out by comparison of the double sequence to the sequence of lysozyme. The search was performed as described previously for SAVINASE, except that only matches greater than 50% were calculated. This analysis revealed that the double sequence arose from sequencing from residue 1 and from residue 64 of the protein. Residue 63 of lysozyme is tryptophan. Thus the data support the conclusion that treatment of lysozyme with the appropriate level of hypochlorite resulted in polypeptide chain cleavage at tryptophan residues.

Analysis of the lysozyme sample arising from treatment with 400 mM bleach revealed many peptide species upon fractionation on Sephadex ®. Sequence analysis of the smallest of these pools again revealed a multiple sequence. Another homology search was performed and this time the search revealed that the sequences arose from degradation of the protein starting at residues 1, 29, 109 and 112. This indicated that cleavages took place at residues 28, 108 and 111, all of which are occupied by tryptophan. These fragments did not separate under the conditions used because four disulfide bonds that are present in lysozyme would hold the fragments together during purification, but would not prevent their degradation during sequence analysis. Again, it is important to note that complete cleavage of lysozyme at all tryptophan residues would create amino termini at residues 1, 29, 64, 109, 112, and 124. Cleavage of lysozyme by bleach results in the creation of amino termini at residues 1, 29, 64, 109 and 112. This is an excellent confirmation of the fact noted with APL and SAVINASE, namely that polypeptide chain cleavage by hypochlorite takes place at tryptophan residues.

EXAMPLE 4

Detergent Use

A bleach stable alkaline protease prepared by the method of this invention can be used as a detergent additive with the anionic/nonionic mixed detergents commonly available on the market. When added to a stock detergent base such as American Home Appliance Manufacturers Association (AHAM) standard phosphate-containing formulation, it will produce an enzyme/detergent mixture which can be used in washing with chlorine bleach, such as Clorox ®, at normal use concentrations up to about 3 mM. Such a detergent mixture would provide increased stain removal capability.

Many modifications and variations can be made to the practice of the present invention without departing from the spirit and scope thereof which is solely defined by the claims.

What is claimed is:

1. An improved *Bacillus licheniformis* alkaline protease, wherein at least one tryptophan has been genetically substituted by tyrosine or phenylalanine, whereby said protease is made stable against cleavage by hypochlorite at said residue.

2. The alkaline protease of claim 1, wherein the alkaline protease is isolated from *Bacillus licheniformis.*

3. The alkaline protease of claim 1, wherein the alkaline protease, prior to substitutions, is APL, as set forth in FIG. 3.

4. A bleach stable detergent composition comprising improved *Bacillus licheniformis* alkaline protease, wherein at least one tryptophan has been genetically substituted by tyrosine or phenylalanine, whereby said protease is made stable against cleavage by hypochlorite at said residue.

5. The bleach stable detergent of claim 4, wherein the alkaline protease is isolated from *Bacillus licheniformis.*

6. The bleach stable detergent of claim 4, wherein the alkaline protease, prior to substitution, is APL, as set forth in FIG. 3.

* * * * *

UNITED STATES PATENT AND TRADEMARK OFFICE
CERTIFICATE OF CORRECTION

PATENT NO. : 5,118,623

DATED : June 2, 1992

INVENTOR(S) : Boguslawski, et al.

Figure 3:
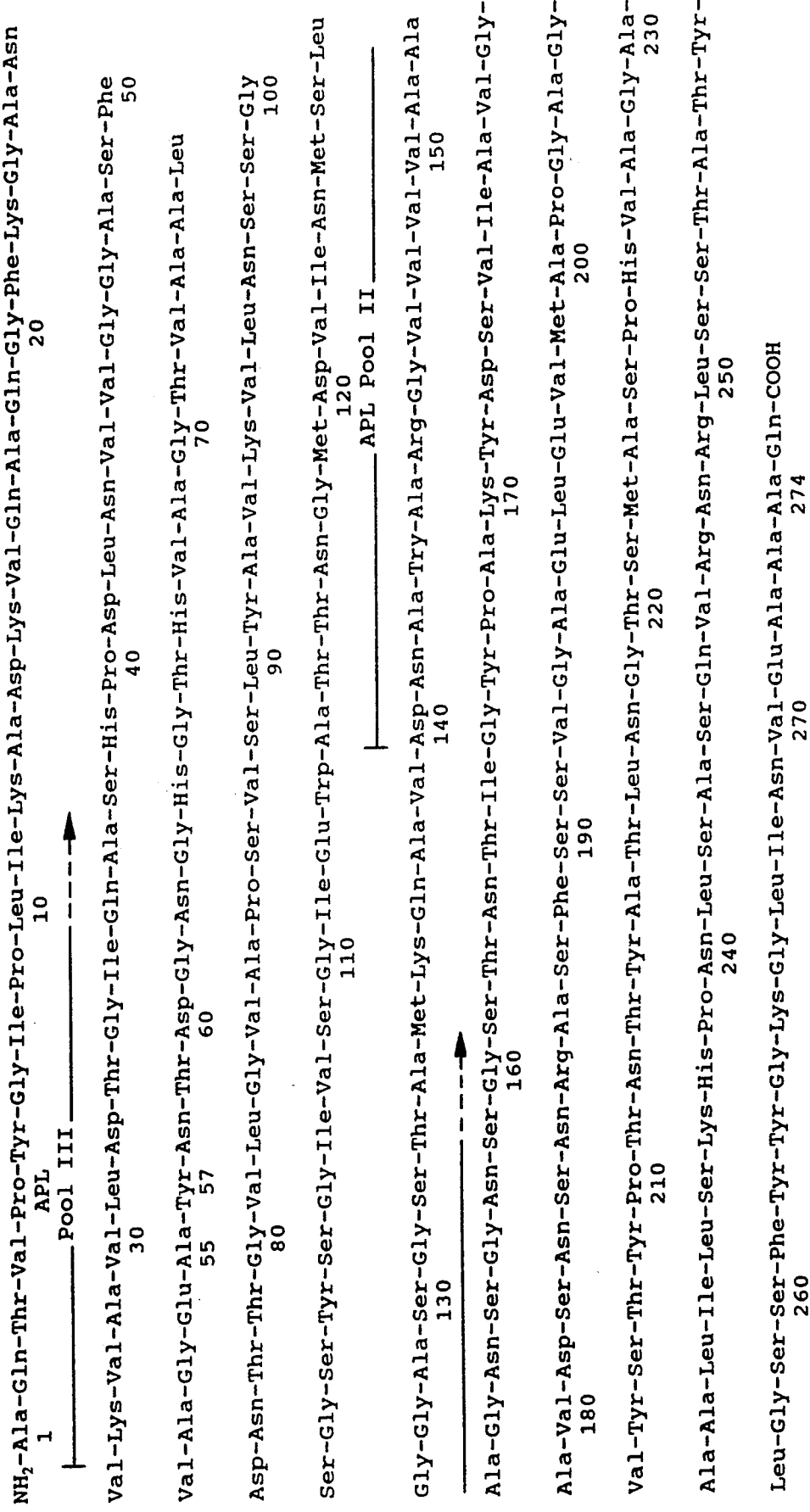
FIG. 3 describes the location of hypochlorite-generated fragments in the sequence subtilisin Carlsberg (APL).

It is certified that error appears in the above-identified patent and that said Letters Patent is hereby corrected as shown below:

At column 3, line 56, change "FIG. 1" to --FIG. 3--.

Signed and Sealed this

Thirtieth Day of November, 1993

Attest:

BRUCE LEHMAN

Attesting Officer

Commissioner of Patents and Trademarks